(12) United States Patent
Vesey et al.

(10) Patent No.: US 6,780,581 B2
(45) Date of Patent: Aug. 24, 2004

(54) PRODUCTS COMPRISING QUANTUM OF BIOPARTICLES AND METHOD FOR PRODUCTION THEREOF

(75) Inventors: Graham Vesey, Gladesville (AU); Mark Gauci, Fairlight (AU)

(73) Assignee: BTF Pty Ltd, New South Wales (AU)

( * ) Notice: Subject to any disclaimer, the term of this patent is extended or adjusted under 35 U.S.C. 154(b) by 0 days.

(21) Appl. No.: 09/949,860

(22) Filed: Sep. 12, 2001

(65) Prior Publication Data

US 2003/0049717 A1 Mar. 13, 2003

(51) Int. Cl.⁷ ............................ C12Q 1/70; C12Q 1/00; C12N 7/02; G01N 33/53; G01N 33/48
(52) U.S. Cl. ................................ 435/5; 435/4; 435/7.1; 435/7.2; 435/239; 436/63; 436/260; 436/518; 436/523; 436/546
(58) Field of Search ........................ 435/4, 5, 7.1, 7.2, 435/239; 436/63, 260, 518, 523, 546

(56) References Cited

U.S. PATENT DOCUMENTS

| | | | |
|---|---|---|---|
| 3,655,838 A | | 4/1972 | Prile et al. |
| 3,932,943 A | | 1/1976 | Briggs et al. |
| 4,243,687 A | | 1/1981 | Kline ............................ 426/62 |
| 5,700,691 A | * | 12/1997 | Bender et al. ............... 435/325 |
| 6,106,836 A | | 8/2000 | Wilderbeek et al. |
| 6,225,046 B1 | * | 5/2001 | Vesey et al. .................... 435/5 |

FOREIGN PATENT DOCUMENTS

| | | |
|---|---|---|
| EP | 0 145 197 | 9/1989 |
| WO | WO 01/09281 A1 | 2/2001 |
| WO | WO 01/68902 A1 | 9/2001 |

OTHER PUBLICATIONS

Webster's Ninth New Collegiate Dictionary. 1986. p. 963.*
Simlone, F.P. et al. ATCC Preservation Methods: Freezing and Freeze Drying, Second Edition, 1991, pp. 27–28.*

Howard M. Shapiro, "Flow Cytometry in Laboratory Microbiology: New Directions," American Society for Microbiology News, 1990, pp. 584–588, vol. 56, No. 11.

J.D. Mellor, "Fundamentals of Freeze–Drying,"pp. 3–15 and 329–337, Academic Press, London (1978).

Georg–Wilhelm Oetjen, Freeze–Drying, pp. 201–227 and 253–266, Wiley–VCH, Weinheim (1999).

Howard M. Shapiro, M.D., "Practical Flow Cytometry," pp. 217–228, third edition, A R Liss, New York.

International Search Report for Corresponding PCT App. No. PCT/AU02/01216.

Van Noorden (1991) Histochemical Journal, 23: 429–435.

Peterz et al. (1993) Journal of Applied Bacteriology, 74: 143–148.

Champagne et al. (2000) Journal of Applied Microbiology, 88: 124–131.

Malucelli et al, (1995) Vaccine, 13 (3): 273–275.

Pembrey et al. (1999) Appl. Environ. Microbiol., 65 (7): 2877–2894.

Meo et al. (1998) Arch Microbiol, 170: 339–344.

Kairo et al. (1999) Vaccine, 17: 2425–2428.

* cited by examiner

*Primary Examiner*—Jon P. Weber
*Assistant Examiner*—Kailash C. Srivastava
(74) *Attorney, Agent, or Firm*—Morgan, Lewis & Bockius LLP

(57) ABSTRACT

A method for the production of a product containing a quantum of bioparticles, for example bacterial cells, is provided, as are products obtained thereby. In one embodiment, the products contain a defined quantum of bioparticles, preferably presented in a viable state. Products made in accordance with the invention may be usefully put to applications where having knowledge of the number of bioparticles present may be important or at least advantageous.

32 Claims, No Drawings

PRODUCTS COMPRISING QUANTUM OF BIOPARTICLES AND METHOD FOR PRODUCTION THEREOF

FIELD

The present invention relates to a method for the preparation of products containing a quantum of bioparticles, preferably viable bioparticles, and to said products produced thereby. More particularly, the invention relates to a method for the preparation of products containing a defined quantum of bioparticles, and to said products produced thereby.

BACKGROUND

There are many procedures performed in life sciences that involve the manipulation of small bioparticles such as cells, bacteria, viruses, protozoa, sperm, eggs, embryos and larvae. Generally the manipulation of these small bioparticles is inherently difficult because the bioparticles are too small to be visualised with the naked eye.

Where one is performing an experiment or procedure that involves adding bioparticles to a vessel (for example, a test tube) there is currently no simple technology available which allows one to know exactly, or at least with a minimal degree of error, how many bioparticles have been added. Typically one would prepare a suspension of the bioparticles and then perform an analysis (for example, enumeration by microscopy or culture on an agar plate), to estimate the number of bioparticles per volume of fluid. An aliquot of this suspension, containing an estimated number of bioparticles, would then be used for a desired purpose; the exact number of bioparticles in the aliquot not being known.

In addition to problems associated with estimation of the numbers of bioparticles by sampling, further problems may result during manipulation of the bioparticles in a particular procedure. For example, an unknown amount of the bioparticles are inevitably lost due to factors such as adhesion to surfaces of vessels or pipettes used, or to denaturation or death of some of the bioparticles. Further, bioparticles can lose their viability over time and accordingly products containing such particles may suffer from a short shelf life. Combined with the above problems, these factors may create gross inaccuracies in experimental data.

A number of products are known which attempt to provide a standardised product having a defined number of bioparticles. However, these products unfortunately fail to address all of the problems above mentioned, and accordingly, may be considered to fall short of providing a desirable product. For example, the degree of error in respect of the number of bioparticles present from one sample of a product to another sample of the same product is likely to be in the order of greater than 50%, in many cases the number of bioparticles present may vary 10 to 100 fold or more.

One example of such known products is Cultiloops® (Oxoid, Australia). Cultiloops® are disposable bacteriological culture loops that contain a loopful of freeze-dried culture of a specific microorganism and are generally used for quality control purposes in microbiology laboratories. While Cultiloops® save time in the preparation of cultures for quality control they unfortunately do not contain accurately defined numbers of cells per loopful. Further, it is possible that a number of the cells present may not be in a viable state.

Several companies supply vials containing an approximate number of microorganisms in a freeze-dried form. Typically, these are manufactured to an accuracy of 1 order of magnitude; for example, a vial will contain between 1000 and 10000 bacteria. To use these products one generally adds water to the vial to resuspend the freeze-dried microorganisms, subsequently using a pipette to transfer the microorganisms to a sample. Due to the nature of this product, and the means by which it is used, it may not be considered to adequately address the issue of providing accurate and consistent numbers of bacteria, or the issue of the loss of unknown quantities of bacteria during manipulation as a result of adhesion to the side of the vial or the pipette.

BTF Pty Ltd (Australia) market a product known as EasySeed C&G that provides an accurately defined number of inactivated Cryptosporidium and Giardia in fluid in a test tube. While it may be considered that this product overcomes many of the issues associated with providing accurate numbers of microorganisms, during use of the product an unknown number of the Cryptosporidium and Giardia are generally lost due to adhesion to the side of the test tube or pipette. Further, the cells are not provided in a viable state.

A further example of a presently available product are lenticles, freeze-dried quality control samples prepared by the UK Public Health Laboratory Service (PHLS). Lenticles are prepared by pipetting drops of a viscous bacterial culture onto a cold surface, freezing the drops, and then freeze-drying the drops to form a lens-shaped freeze-dried pellet. While the lenticules may be considered to overcome the inaccuracies associated with handling liquid quality control samples, they unfortunately do not contain accurately defined numbers of bacteria.

A further product, known as TrueCount® (Becton Dickinson, San Jose, USA), is used in conjunction with flow cytometry to allow one to determine the number of specific cells per milliliter of blood, for example. The product consists of dried balls of approximately 1 mm diameter that contain approximately 50,000 fluorescent beads of approximately 5 $\mu$m diameter. While this product may overcome problems associated with the loss of particles during manipulation of a liquid sample, it does not contain an accurately defined number of beads within the dried ball. Further, as the beads do not represent biological material, the product, and the procedure of producing the same, is not concerned with, and therefor may not adequately address, the issue of maintenance of viability of the particles.

U.S. Pat. No. 3,932,943 describes a process for the production of a homogeneous, lyophilised particulate product containing at least one biologically active component. The process involves spraying a solution or colloidal suspension containing the biologically active component into a moving bath of fluorocarbon refrigerant, subsequently lyophilising the resultant frozen droplets. The inventors report that the product has a spherical shape, free-flowing properties, and rapid dissolution times. However, the process does not address the issue of preparing a product that contains accurately defined numbers of bioparticles. In addition, it may be considered that this process does not adequately address the issue of maintenance of bioparticle viability, especially where such bioparticle is a cell. U.S. Pat. No. 6,106,836 describes a process for the production of a vaccine product comprising a container with freeze-dried vaccine components therein. The process involves the formation of spheres containing biological components of estimated numbers utilising the steps of freezing droplets of a suspension containing the biological components in a cryogenic liquid and subjecting them to freeze-drying. The process of this patent does not immediately address the issue of preparing a freeze-dried product that contains accurate numbers of bioparticles. By contrast, products containing estimated numbers of components are made via the above mentioned process, their titre measured, and then a number of products combined, or used to supplement another product, to obtain a desired quantity of components. In addition, the process of U.S. Pat. No. 6,106,836 may not be considered to adequately address the issue of maintenance of the viability of bioparticles during processing; rather, the process centres on the loss of viability of the bioparticles followed by supplementation of the resultant product with additional viable particles.

Further, U.S. Pat. No. 3,655,838 describes a method for the preparation of pelletised reagents purportedly in a stable, accurate form. In this method a suspension containing predetermined concentrations of desired reagents is formed into calibrated droplets which are allowed to fall into a liquid having certain characteristics, one of which is a temperature gradient suitable to freeze the droplets. Subsequently, the droplets are dried to form the pelletised product. While the method aims to provide products containing predetermined and pretested measured amounts of certain reagents, it may be considered to suffer from inaccuracies in the actual concentration or number of specific components present, due to methods employed to arrive at initial concentration values. Further, the method may be considered not to accurately address the issue of maintenance of viability where the reagent to be processed is a bioparticle.

SUMMARY OF INVENTION

The inventors have devised a method which surprisingly allows for the preparation of a freeze-dried product containing a quantum, particularly a defined quantum, of bioparticles in a stable format that can be easily manipulated while minimising the loss of any of the said bioparticles. The method is particularly applicable to the formation of a product comprising viable bioparticles. It is believed that the nature of the product according to the invention will allow for simplified manipulation of bioparticles and for more accurate and reproducible results from procedures utilising bioparticles.

Accordingly, in one broad aspect of the present invention there is provided a method for the preparation of a product comprising at least a defined quantum of bioparticles, said method comprising the steps:

Providing a sample of bioparticles;
Analysing said sample of bioparticles to identify desired bioparticles of a predetermined nature;
Selecting a defined quantum of desired bioparticles;
Forming frozen spheres containing said defined quantum of desired bioparticles;
Freeze-drying the frozen spheres to form the product.

Preferably, one freeze-dried sphere is formed per defined quantum of desired bioparticles to form the product. Alternatively, two or more freeze-dried spheres are formed per defined quantum of desired bioparticles to form the product.

Preferably, the analysis of said sample of bioparticles is conducted using flow cytometry technology. Preferably, the selection of a defined quantum of desired bioparticles is also conducted using flow cytometry technology.

Preferably said frozen spheres are formed by dropping a volume of liquid containing the defined quantum of viable bioparticles into a cryogenic liquid. Preferably, said cryogenic liquid is liquid nitrogen.

Preferably, the method also comprises a final quality control step. Preferably the quality control step involves one or more of:

counting the number of bioparticles contained within a number of products;
measurement of the uniformity of the product, by weighing or measuring the size of a number of products.

In another broad aspect of the present invention, there is provided a product comprising at least a defined quantum of bioparticles made in accordance with the method described herein before. Preferably the bioparticles are viable.

Preferably, the product comprises a single freeze-dried sphere comprising bioparticles. Alternatively, the product comprises two or more freeze-dried spheres.

Preferably, said defined quantum of bioparticles comprises a single species of bioparticle. Alternatively, said defined quantum of bioparticles comprises a mixture of two or more species of bioparticle.

Preferably, each freeze-dried sphere of said product additionally comprises supplementary agents. Preferably, said supplementary agents are those which aid in maintaining the viability of the bioparticles. More preferably, said supplementary agents are cryopreservatives.

In another broad aspect of the present invention there is provided the use of a product herein before described.

In an alternative broad aspect of the present invention there is provided a method for the preparation of a product comprising at least a quantum of bioparticles, said method comprising the steps:

Providing a sample of bioparticles;
Selecting a quantum of bioparticles;
Forming frozen spheres containing said quantum of bioparticles;
Freeze-drying frozen spheres to form the product.

Preferably, one freeze-dried sphere is formed per quantum of desired bioparticles to form the product. Alternatively, two or more freeze-dried spheres are formed per quantum of desired bioparticles to form the product.

Preferably, the method described in the two immediately preceding paragraps further comprises the step of analysing said sample of bioparticles to identify desired bioparticles having of a predetermined nature, prior to the step of slecting a quantum of bioparticles.

Preferably, the method of the three immediately preceeding paragraphs also comprises a final quality control step. Preferably the quality control step involves one or more of:

counting the number of bioparticles contained within a number of products;
measurement of the uniformity of the product, by weighing or measuring the size of a number of products.

The invention may also be said broadly to consist in the parts, elements and features referred to or indicated in the specification of the application, individually or collectively, in any or all combinations of two or more of said parts, elements or features, and where specific integers are mentioned herein which have known equivalents in the art to which the invention relates, such known equivalents are deemed to be incorporated herein as if individually set forth.

PREFERRED EMBODIMENT(S)

These and other aspects of the present invention, which should be considered in all its novel aspects, will become apparent from the following description of the preferred forms of the invention given in general terms. The invention will be further elucidated from the non-limiting Examples provided hereafter.

The invention relates to a process for preparing a product which contains at least a quantum of bioparticles, preferably a defined quantum, of bioparticles. The product of the invention generally comes in the form of a single freeze-dried mass, preferably a ball. However, the inventors contemplate the product comprising a group of balls, preferably 3 to 10 balls, which taken together provide the quantum, preferably defined quantum, of bioparticles. While the following description focuses on the embodiment of the invention in which the product represents a single ball, it will be appreciated by skilled persons that the description may be readily read to encompass the embodiment in which the product comprises a group of balls.

In order to facilitate manipulation of the product following formation thereof, the ball is preferably large enough to be visible to the human eye. Accordingly, the balls of the invention are preferably 0.1 to 10 mm in diameter, and more preferably 4 mm. However, it will be appreciated that the balls may be of a diameter larger than 10 mm, or of a diameter smaller than 0.1 mm.

As used herein, the term "bioparticles" refers to particles of a biological nature. Such bioparticles may preferably be cells, of prokaryotic or eukaryotic origin, or alternatively, proteins or cell organelles such as nuclei. Accordingly, bioparticles which may be applicable to the invention include, bacteria, fungi, yeast or virus, single or multi-cellular protozoa, or prions. Examples of such bioparticles include Cryptosporidium, Giardia, Cyclospora, Toxoplasma, Eimeria, Legionella, Salmonella, Leptospirosis, Escherichia, Saccharomyces, Clostridium, Vibrio, Pseudomonas, Anthrax, Bacillus, Streptomyces, Staphylococcus, blood cells, HIV, Norwalk virus, herpes simplex virus. A product according to the invention may comprise a single species of bioparticle, or alternatively, two or more species of bioparticle.

As previously mentioned herein, the invention is particularly applicable to the formation of a product comprising viable bioparticles. As used herein "viable bioparticles" are those particles capable of working, functioning, or developing substantially as in their native state, or a state to which they have been designed to have via laboratory manipulation. Accordingly, in the case of cells, "viable bioparticles" are those particles capable of, for example, functioning, growing, developing and, where applicable, infecting a host.

As used herein a "quantum" of bioparticles refers to the number of bioparticles present, or desired to be present, within the product of the invention. A "quantum" does not imply that exact numbers of bioparticles will be present within a sample or product according to the invention. Generally, "quantum" of bioparticles, refers to the number of bioparticles estimated to be present via conventional means used in the art; for example, enumeration by microscopy. It should be appreciated that the term "a quantum" generally relates to the aspect of the invention described under the heading "alternative embodiment" herein after.

According to the invention, a "defined quantum" of bioparticles, is the number of bioparticles present within the product of the invention. Preferably, a "defined quantum" represents an exact number of bioparticles. However, the inventors contemplate a minimal degree of error in respect thereof; for example, a degree of error of approximately 35% or less of the total, preferably 10% or less, and more preferably 5% or less. The inventors believe such error may be monitored and minimised by conducting quality control checks of the products formed in the method of the invention, as herein after described.

It will be appreciated that the number of bioparticles selected to be present within the product of the invention may vary depending on the nature of the bioparticles to be processed, the desired size of the final product (the freeze-dried balls), and the ultimate use to which the final product will be put. For example, freeze-dried balls containing E. coli, which are desired to be used in quality control of microbiology culture media will preferably contain 30 viable E. coli cells. In addition, a product according to the invention may comprise a single species of bioparticles, or alternatively, a mixture of two or more specific species of bioparticles.

The product, or balls, of the present invention, preferably contain constituents in addition to the quantum of bioparticles. Said "constituents" will generally comprise those components of the media in which the bioparticles were grown or suspended in prior to processing according to the invention; such constituents will be readily recognised by persons of general skill in the field, and will become further apparent from the description of the method of the invention to follow. The product or balls of the invention may additionally contain supplementary agents which may have been introduced thereto during processing, or added to the growth or suspension media in which the bioparticles were initially prepared.

"Supplementary agents" are those agents which may aid in the preservation of the viability of the bioparticles during processing (for example, cryopreservatives such as glycerol or dimethyl sulfoxide (DMSO), antioxidants such as activated charcoal, sugars such as glucose), or alternatively, which may be desired to be present in the final product based on a particular application to which it will be put; for example, a dye may be added so that when the freeze dried ball is added to a liquid sample a colour change of the sample will occur, a detergent may be added to assist with rehydration, or common bulking agents may be used to help give body to the resultant balls of the invention. Such agents may be introduced at various stages of the method of the invention, however it is preferable that they be added at the initial stage of preparing the bioparticles (described herein below).

The inventors particularly contemplate the presence of cryopreservative agents within the balls of the invention. Such appropriate cryopreservative agents, which are well known in the art, include: glycerol, which may be used at a concentration of between 1 and 20% (v/v), or dimethyl sulfoxide (DMSO), which may be used at a concentration of between 1 and 20% (v/v).

The inventors also contemplate the presence, within the balls of the invention, of protective agents that assist the survival or maintenance of the viability of the bioparticles during the drying process. Such appropriate protective agents include activated charcoal, honey, sodium glutamate, raffinose and animal serum; skilled persons may be able to identify further appropriate protective agents. These protective agents may be used at concentrations of between 1 and 30%, for example.

It will be appreciated that the cryopreservative and the protective agent used in the invention may be varied so as to obtain the most optimal conditions for the particular bioparticle to be processed. By way of example, where the bioparticles represent bacteria such as E. coli appropriate cryopreservatives include glycerol and DMSO and appropriate protective agents include activated charcoal.

First Preferred Embodiment

This preferred embodiment of the invention is described in terms of the formation of a product comprising a single ball comprising a defined quantum of bioparticles. It should be appreciated however, that the embodiment is readily applicable to a product comprising a group of balls, which taken together provide the defined quantum of bioparticles.

In general terms, the most preferred method of arriving at the freeze-dried balls of the invention comprises the following steps:

1. Preparation of bioparticles;
2. Analysis of bioparticles;
3. Selection (or sorting) of a defined quantum of bioparticles;
4. Creation of frozen spheres containing bioparticles;
5. Freeze-drying of spheres to form balls; and optionally
6. Quality control of the freeze-dried balls.

1. Preparation of Bioparticles

The first step of the method of the invention involves preparing and providing a sample of bioparticles in a liquid suspension media.

Generally, the bioparticles will be prepared according to methodology well known in the technical field to which the invention relates. For example, in the case of prokaryotic or eukaryotic cells, the cells may be grown in an appropriate growth media (for example, nutrient broth (Oxoid, Australia) in the case of *E. coli*) to a desired density. In any case, it will be appreciated that standard texts referred to in the art will provide information of appropriate means for providing various bioparticles of use in the invention.

As will be appreciated, the liquid suspension media referred to above will vary depending on the nature of the bioparticles to be processed, and the ultimate use to which the product of the invention will be put. For example, where the bioparticles represent cells, the media in which they have been grown may represent the suspension media. Alternatively, in the case of cells, they may be harvested from their growth media and resuspended in an alternative media, which may be more suitable, having regard to the use to which the final product will be put. In any case, those persons of skill in the art may readily be able to identify suitable suspension medias for a particular bioparticle based on well-known principles in the art and by reference to standard texts.

The preparation of bioparticles should preferably aim to maximise maintenance of viability of the bioparticles throughout the subsequent manufacturing process. Skilled persons will be able to recognise such conditions. However, by way of general example, the optimisation of conditions at this stage of the manufacturing process may involve growth of the bioparticles under specific conditions that enhance the robustness thereof; growth of the bioparticles to a particular stage of growth known, or found, to be optimal for survival of a particular bioparticle; exposure of the bioparticles to conditions such as starvation or heat shock. By way of specific example: *E. coli* cells that are in the stationary growth phase will maintain their viability better than cells in logarithmic growth phase; bacteria such as Legionella may better maintain viability through the manufacturing process if they have been starved for several days by storage in distilled water.

The inventors contemplate that maintenance of the viability of the bioparticles during subsequent processing in the invention, may be enhanced via introducing supplementary agents to the growth and/or suspension media within which the bioparticles may be grown and/or suspended. The addition of supplementary agents to the growth and/or suspension media for alternative reasons is also contemplated by the inventors. Suitable supplementary agents are described herein before.

In addition, the inventors contemplate that the bioparticles may be modified during the initial preparation step. Such modification may, for example, enhance subsequent analysis and sorting or alternatively, may provide desirable characteristics suited to the ultimate use to which the product of the invention will be put. For example, cells may be in recombinant form, or may be labelled or tagged with suitable agents (for example, antibodies, fluorescent stains such as fluorescein diacitate (FDA), propidium iodide (PI), oligonucleotides).

2. Analysis of Bioparticles

The second step of the manufacturing process of this preferred embodiment of the invention involves the analysis of the liquid sample containing the bioparticles using flow cytometry techniques known in the art (Shapiro, 1990; 1995). By using such technology, desired particles may be identified. Such "desired particles" are particles of a predetermined nature. For example, a particular cell type which may be present in a background of alternative bioparticles, or those cells of a certain type which are viable. As will be appreciated, the technique of flow cytometry may be used to analyse bioparticles based on preselected physical characteristics; for example, absorption at a particular wavelength, density, magnetism, specific gravity, impedance, ability to scatter light, luminescence, or fluorescence. In addition, the inventors contemplate the use of Coulter sensing and raman microscopy in conjunction with flow cytometry to analyse and sort bioparticles according to the invention.

While a single specific preselected characteristic of a particular bioparticle may be used for analysis thereof in this step of the manufacturing procedure of the invention, the inventors contemplate the use of multiparameter flow cytometry. "Multiparameter flow cytometry" is used herein to mean the measurement of several characteristics of a particular particle to differentiate it from another.

The techniques available to analyse bioparticles using flow cytometry are well documented in the art. However, by way of exemplification, where one wishes to rely on optical analysis, a sample containing bioparticles may be mixed with one or more dyes, fluorescent or luminescent agents, or antibodies conjugated to such agents, for example, prior to analysis via flow cytometry so that specific bioparticles are stained or tagged. An example of such a process involves the use of the dye fluorescein diacitate which specifically stains viable cells. Following staining with fluorescein diacitate, the sample may be analysed and single viable bioparticles that are at a specific stage of their life cycle identified.

3. Selection of Bioparticles

In accordance with the present embodiment of the invention, following step 2, or simultaneously therewith, the desired particles may be selected, or sorted, from the sample, on the basis of the preselected characteristics mentioned herein before, and in accordance with flow cytometry technology. Utilising the flow cytometer, a defined quantum of a desired particle, or particles, may be sorted.

In accordance with this step of the manufacturing process, following the identification and counting of a defined quantum of bioparticles, the flow cytometry apparatus may express a volume of liquid containing the same. Preferably, the apparatus is configured such that the liquid containing a defined quantum of the bioparticles is forced through an orifice in a downward direction so that a droplet is formed. The size of the orifice can be changed to precisely control the volume of the droplet.

While the above technique is considered by the inventors to be the most preferred means for particle sorting and formation of a volume of liquid comprising a defined quantum of selected particles, it is contemplated that alternative means known in the art may be used. For example, the invention may employ piezo capillary dispensing, a piezo-actuated catcher tube, charged droplet deflection, acoustic manipulation (Standing Wave, Shock Wave), electrostatic manipulation, and optical tweezers. Those of general skill in the art may realise further techniques readily applicable to the present invention.

The inventors contemplate the fluid output from the cytometer being mixed with supplementary agents prior to dropping the droplets into a cryogenic liquid. Some supplementary agents may interfere with the analysis and sorting of the bioparticles if they are added into the flow cytometer sheath fluid; for example, activated charcoal and dyes such as malachite green. By introducing supplementary agents at this stage of the procedure, this problem may be overcome.

4. Creating Frozen Spheres.

In this step of the process, the droplets formed in step 3 above are dropped into a vessel that contains a cryogenic liquid, preferably liquid nitrogen, resulting in the formation of frozen spheres that contain a defined quantum of selected bioparticles.

This freezing step is preferably performed at a temperature that is optimal for the preservation of the viability of the bioparticles. It will be appreciated that the optimal temperature may vary depending on the nature of the bioparticles being prepared. However, those of general skill in the art will readily be able to determine the optimum temperature range by performing experiments at a range of different temperatures and comparing the numbers of bioparticles that survive the freezing process. Accordingly, while the use of liquid nitrogen is preferred, it will be appreciated that a number of alternative cryogenic liquids may be employed in the invention in order to satisfy a particular temperature requirement. For example, liquid helium and liquid oxygen. Persons skilled in the field of technology to which the invention relates will readily be able to identify the most appropriate cryogenic liquid to be used based on the temperature requirements of a particular bioparticle. In addition, the temperature of the cryogenic fluid could be controlled by adjusting the pressure of the cryogenic fluid.

5. Freeze-Drying.

In accordance with the present invention, the frozen spheres formed in step 4 above are then freeze-dried. Freeze-drying may be conducted according to standard procedures; (Oetjen 1999; Rowe 1978; Mellor 1978).

As it will be appreciated, it is desirable that this step be conducted in a manner which maintains the viability of the bioparticles. Of course, such conditions may vary depending on the nature of the bioparticles being prepared. However, a person of general skill in the art will readily be able to determine the most effective conditions based on the teachings of Oetjen (1999), Rowe (1978), and Mellor (1978).

6. Optional Quality Control

The inventors contemplate the use of a quality control (QC) step following the formation of the product as above described. Such quality control steps may allow for the minimisation of error in the number of bioparticles present within the balls and/or the size of the products produced. Such QC steps may involve either counting the number of bioparticles contained within selected samples of the product by analytical methods such as culturing the bioparticles on agar plates, or by flow cytometry, or by nucleic acid based analytical methods such as the polymerase chain reaction (PCR) within selected samples of the product, or measurement of the uniformity of the product, for example by weighing or measuring the size of selected balls.

Following formation in accordance with the invention, the balls may be packaged and stored in a test tube, vial or similar container. Alternatively, the balls can be packaged in blister packs similar to those used for tablets. The balls are preferably stored under conditions that minimise the exposure of the balls to oxygen and humidity, including, for example, storage under vacuum or storage under inert gasses such as nitrogen or argon. Alternatively, a dehumidifying agent such as silica gel can be packaged with the balls. The balls can be packaged individually or in groups. For example, a ball that contains 10 $E.$ $coli$ cells can be packaged in groups of ten so that each package contains 100 $E.$ $coli$ cells.

Subsequently, the balls may be put to use in a particular application by opening the package that contains the ball and then tipping the container upside down so that is preferably mixed or agitated to assist with rehydration of the ball. Where the ball is added to a dry sample, such as the surface of an agar plate, then a volume of fluid such as water may be added to the plate to rehydrate the ball. In the case of the ball being contained in a vessel such as a vial or test tube, a sample of fluid may be added to the vessel and the experimentation or analysis to be conducted carried out in such vessel. While not as preferable, the invention also contemplates the addition of a fluid to the packaging followed by transfer of the sample, containing the rehydrated ball, to an appropriate vessel.

The freeze-dried product prepared according to the invention may be suitable for use in a number of commercial and/or research applications (for example, applications pertaining to microbiology, molecular biology, cell biology, biochemistry, biotechnology, medicine, and the food and beverage industry), especially in those applications where it is desirable to have control over the number of bioparticles present.

One particular application to which the balls of the invention may be put is in the testing of water samples for the presence of $E.$ $coli$. Traditionally, during such testing, quality control (QC) steps are conducted, which involve adding a known number of $E.$ $coli$ to a water sample and then analysing the same. Current protocols for preparing a QC sample involve preparing a suspension of $E.$ $coli$ and then performing an analysis to estimate the number of $E.$ $coli$ per ml of fluid. An aliquot of this suspension is then used in the testing procedure. As it will be appreciated, this known procedure may suffer from experimental artefacts due to the fact that one cannot determine with accuracy the exact number of cells present in the sample used, and also based on the loss of cells due to adhesion to surfaces of manipulation apparatus, such as pipettes. Alternative techniques involve a water sample being seeded with a freeze-dried sample of $E.$ $coli$. These freeze-dried $E.$ $coli$ samples, which are commercially available, do not contain accurate numbers of $E.$ $coli$ and are not in a format that can be easily manipulated without loss of $E.$ $coli$ cells due to adhesion of cells to surfaces. The use of the balls of the present invention may introduce accuracy into QC procedures such as these as precise numbers of organisms will be able to be added to a quality control sample and not lost during manipulation.

A further example of an application to which the balls of the invention may be put is in internal quality control (IQC) techniques used in microbiology. Such techniques are relatively new. One such procedure is described in PCT/AU00/00896 and involves the addition of an exact number of modified microorganisms to a sample before analysis. The microorganisms are modified to ensure that they can be easily differentiated from microorganisms that are present in the sample. For example, a green fluorescent protein (GFP) gene may be inserted into the organisms so that they can be differentiated from microorganisms present in the sample by their fluorescent properties. Use of the balls of the present invention may overcome problems associated with the format in which the modified micro-organisms are presently used; for example, fluid samples, which may contain accurate numbers of a particular modified organism, but unfortunately invariably suffer from loss thereof during manipulation.

The freeze-dried balls of the present invention may also have specific application in delivery systems for oral vaccines. The use of the balls in this application would enable exact numbers of microorganisms to be administered to a subject, with no loss of microorganisms during administration of the vaccine. Similarly, the product of the invention may find application in the delivery of pro-biotics to a subject.

Further, the inventors contemplate the product of the invention to have direct application in the in vitro fertilization (UVF) industry. The product of the invention would enable simple manipulation of precise numbers of sperm cells, embryos and eggs.

The food and beverage industry is also likely to benefit from the use of the balls of the invention, particularly where microorganisms are used as starter cultures. For example, the fermentation of food, beer and wine would benefit from the use of technology that allows addition of exact numbers of microorganisms, allowing the introduction of a greater level of reproducibility in the fermentation process.

Biotechnology processes that involve the growth of cells, bacteria or other bioparticles would benefit from the use of the present technology. For example, the production of recombinant proteins from prokaryotic or eukaryotic cells may often be problematic resulting in differing yields of protein from one culture to another. While problems may stem from a number of factors involved in the culturing, expression, and harvesting process, the fact that a culture is seeded with an inconsistent quantity of recombinant cells may be considered one such problem. Accordingly, seeding an initial culture with a ball of the present invention, which ball contains a defined quantum of the recombinant cells, may alleviate one variable in the process.

EXAMPLE 1

Preparation of *E. coli*

A strain of *E. coli* (ATCC 11775) was grown in nutrient broth (Oxoid, Australia) at 37° C. for 12 hours. The sample was diluted 1 in 1000 into filtered (0.22 $\mu$m) PBS.

Analysis of *E. coli*

The sample of *E. coli* was analysed using a Becton Dickinson FACScalibur flow cytometer. The cytometer was used generally in accordance with the manufacturers recommendations and using the following parameters: the sheath tank was filled with sterile nutrient broth (Oxoid, Australia) plus 5% glucose; the cytometer was used with the detectors set at the following levels of sensitivity:

Forward scatter E002
Side scatter 500
Side scatter was used as the Threshold at a value of 350.

A region was defined on a scatter plot of Side scatter verses Forward scatter that contained the *E. coli*. This region was then used to sort the *E. coli*.

Selection of Desired *E. coli*

The cytometer was set, according to the manufacturers instructions, to sort samples of 30 *E. coli* cells. The flow rate and the concentration of the *E. coli* were adjusted to ensure that the sort rate was between 150 and 200 sorts per second.

Freezing and Freeze-Drying the Droplets

Droplets were collected into test tubes that contained liquid nitrogen. After collection of the droplets the tubes were placed in a Dynavac FD12 freeze dryer and dried overnight at a vacuum of 2×10−1 Torr and a condenser temperature of −70° C.

The next day, the freeze-dried balls were removed from the freeze drier and individually placed onto nutrient agar plates (Oxoid, Australia), and 200 $\mu$l of sterile water was carefully pipetted onto each ball. The balls were allowed to rehydrate for 5 min and then spread with a sterile plastic spreader. After incubation at 37° C. for 12 hours the agar plates were examined and were observed to contain between 20 and 25 *E. coli* colonies.

Alternative Embodiment

The technology of the present invention may be put to applications which may not require a defined quantum of the particles, to be present in each ball or within a group of balls. One such example is in oral vaccination applications. In such application balls containing an approximate number of bioparticles (e.g. between 5×10E5 and 1×10E6) may be used.

Accordingly, the inventors contemplate modification of the preferred method of the invention described herein before to allow for the manufacture of a product comprising a "quantum" of bioparticles (as herein before defined), as opposed to a "defined quantum" thereof.

In this embodiment of the invention, the freeze-dried balls of the invention may be prepared substantially in accordance with the process herein before described. However, in this form of the invention, one need not sort or select a "defined quantum" of the bioparticles. In addition, while analysis of the bioparticles within the initial sample may be conducted as previously herein described, in order to provide assurance of the purity of the end product, it is not essential to the present embodiment for this step be conducted.

According to the present embodiment, frozen spheres containing a quantum of bioparticles are formed by allowing droplets of the suspension of bioparticles to fall into a cryogenic liquid as herein before described. The droplets may be formed by forcing an appropriate suspension of bioparticles (pre or post analysis) through any suitable orifice. For example, this step may be performed using a peristaltic pump connected to a pastuer pipette. Those skilled in the art will appreciate alternative means by which such droplets may be formed. Where a flow cytometry apparatus has been employed to analyse and select the bioparticles, quantities of bioparticles may be expressed therefrom by known means.

As with the previously described embodiment of the invention, the droplets which are formed are allowed to fall into a cryogenic liquid to form a frozen sphere of bioparticles.

The frozen spheres contained within the cryogenic liquid may then be subjected to a freeze drying procedure as described previously herein to form the balls of the invention. Freeze-dried balls may be packaged, stored, and prepared for use as previously described herein.

As will be appreciated, suspension and growth media's, temperatures, and other conditions of the process according to the present embodiment of the invention may be optimised to the needs of a particular bioparticle and the application to which the final product may be put. Generally, the conditions should be such that the viability of the bioparticles is maintained during processing.

As with the previously described embodiment of he invention, quality control steps may be conducted post formation of the balls produced in accordance with the present embodiment. In this form of the invention, quality control steps may include: counting the number of bioparticles contained within selected samples of the product by analytical methods such as culturing the bioparticles on agar plates, or by flow cytometry, or by nucleic acid based analytical methods such as the polymerase chain reaction (PCR), or measurement of the uniformity of the product, for example by weighing or measuring the size of selected balls.

The product of this alternative embodiment of the invention may be used in various applications, for example vaccination applications, micro-biological applications, or applications pertaining to molecular biology, where an estimate of the number of bioparticles within the product is sufficient to reach a desired end.

The following examples provides exemplification of the above described "alternative embodiment" of the invention.

EXAMPLE 2

Preparation of E. coli

A strain of E. coli (ATCC 11775) was grown in nutrient broth (Oxoid, Australia) at 37° C. for 12 hours.

Freezing and Freeze-Drying the Droplets

A glass pastuer pipette was used to drop droplets of E. coli broth culture into a beaker of liquid nitrogen. The frozen droplets were collected using a sieve and placed into a chilled (−20° C.) glass freeze-drying vessel.

The frozen droplets were placed in a Dynavac FD12 freeze dryer and dried overnight at a vacuum of $2 \times 10^{-1}$ Torr and a condenser temperature of −70° C.

The next day, the freeze-dried balls were removed from the freeze drier and individually placed into nutrient broth (as detailed herein before). After incubation at 37° C. for 12 hours the tubes were examined and were observed to contain viable cultures of E. coli.

The invention has been described herein, with reference to certain preferred embodiments, in order to enable the reader to practice the invention without undue experimentation. However, a person having ordinary skill in the art will readily recognise that many of the components and parameters may be varied or modified to a certain extent without departing from the scope of the invention. Furthermore, titles, headings, or the like are provided to enhance the reader's comprehension of this document, and should not be read as limiting the scope of the present invention.

The entire disclosures of all applications, patents and publications, cited above and below, if any, are hereby incorporated by reference.

The reference to any prior art in this specification is not, and should not be taken as, an acknowledgment or any form of suggestion that that prior art forms part of the common general knowledge in the field of endeavour.

Throughout this specification, and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

REFERENCES

Mellor, J. D. Fundamentals of freeze-drying. Academic Press, London (1978).
Oetjen, Georg-Wilhelm. Freeze-drying. Wiley-VCH, Weinheim (1999).
Rowe, Terence W. G. Edwards freeze-drying handbook. Edwards High Vacuum, Crawley (1978).
Shapiro, H. M. (1990) Flow Cytometry in laboratory microbiology:new directions. American Society for Microbiology News 56, 584–588.
Shapiro, H. M. (1995) A practical guide to flow cytometry, third edition. A. R. Liss, New York.

What is claimed is:

1. A process for forming a product containing a defined number of microorganisms, the process comprising:

providing microorganisms selected from the group consisting of bacteria, fungi, yeast, virus, protozoa, and mixtures thereof in a suspension;

selecting a defined number of the microorganisms of about 1 to about 1000 from the suspension by a means capable of sensing the microorganisms;

capturing the defined number of microorganisms in a frozen body; and drying the frozen body to produce a product containing the defined number of microorganisms, wherein the product is capable of being transferred between containers in its solid form, wherein the product is capable of releasing the microorganisms in a liquid, and wherein the defined number of microorganisms in the product when measured in two or more replicates is within a degree of error of about 10% or less.

2. The process according to claim 1, wherein the microorganisms are selected from the group consisting of Legionella, Salmonella, Leptospirosis, Escherichia, Saccharomyces, Clostridium, Vibrio, Pseudomonas, Bacillus, Streptomyces, Staphylococcus, and mixtures thereof.

3. The process according to claim 1, wherein the microorganisms are Escherichia coli.

4. The process according to claim 1, wherein the microorganisms are selected from the group consisting of Cryptosporidium, Giardia, Cyclospora, Toxoplasma, Eimeria, and mixtures thereof.

5. The process according to claim 1, wherein the microorganisms are viable in the product.

6. The process according to claim 1, wherein the means capable of sensing the microorganisms is selected from the group consisting of flow cytometer, absorption at a particular wavelength, density, magnetism, specific gravity, impedance, ability to scatter light, luminescence, fluorescence, Coulter sensing, and raman microscopy.

7. The process according to claim 6, wherein the means is a flow cytometer.

8. The process according to claim 1, wherein the microorganisms are captured in a volume from about 0.001 ml to about 1 ml prior to freezing.

9. The process according to claim 8, wherein the volume is from about 0.001 ml to about 0.1 ml.

10. The process according to claim 1, wherein the defined number of microorganisms in the product is within a degree of error of about 5%.

11. The process according to claim 1, wherein the defined number of microorganisms in the product is within a degree of error of about 1%.

12. The process according to claim 1, wherein the product is formed by snap-freezing a volume of liquid containing the defined number of microorganisms and then drying the frozen body to form the product.

13. The process according to claim 12, wherein the snap-freezing is carried out by placing the volume containing the defined number of microorganisms into a cryogenic liquid.

14. The process according to claim 13, wherein the cryogenic liquid is selected from the group consisting of liquid nitrogen, liquid helium, and liquid oxygen.

15. The process according to claim 14, wherein the cryogenic liquid is liquid nitrogen.

16. The process according to claim 15, wherein the cryogenic liquid is placed in a container, a droplet containing the defined number of microorganisms is placed in the container to form the frozen body, and the container holding the frozen body is then subjected to freeze-drying to form a substantially dry solid product in the container.

17. The process according to claim 16, wherein after drying, the container is capped or sealed for storage and transport of the product.

18. The process according to claim 17, wherein in the solid product is a small roundish mass in the form of a ball or sphere.

19. The process according to claim 1, wherein the product contains between about 10 and about 100 microorganisms.

20. The process according to claim 1, wherein the product contains about 30 microorganisms.

21. The process according to claim 1 further including selecting a desired microorganism type from a mixture of microorganism types in the suspension.

22. The process according to claim 1 further comprising adding one or more supplementary agents to the microorganisms.

23. The process according to claim 22, wherein the supplementary agent is selected from the group consisting of cryopreservative agent, glycerol, dimethyl sulfoxide, charcoal, honey, sodium glutamate, raffinose, animal serum, and mixtures thereof.

24. A product comprising at least a defined number of bioparticles made in accordance with the method of claim 1.

25. A product as claimed in claim 24, wherein the bioparticles are viable.

26. A product as claimed in claim 24, wherein the product comprises a single freeze-dried sphere comprising bioparticles.

27. A product as claimed in claim 24, wherein the product comprises two or more freeze-dried spheres comprising bioparticles.

28. A product as claimed in claim 24, wherein the defined number of bioparticles comprises a single species of bioparticle.

29. A product as claimed in claim 24, wherein the defined number of bioparticles comprises a mixture of two or more species of bioparticle.

30. A product as claimed in claim 24, wherein each freeze-dried sphere of said product additionally comprises supplementary agents.

31. A product as claimed in claim 30, wherein the supplementary agents are those, which aid in maintaining the viability of the bioparticles.

32. A product as claimed in claim 30, wherein the supplementary agents are cryopreservatives.

* * * * *